United States Patent
Caturla Javaloyes et al.

(10) Patent No.: US 7,582,676 B2
(45) Date of Patent: Sep. 1, 2009

(54) 2-PHENYLPYRAN-4-ONE DERIVATIVES AS SELECTIVE COX-2 INHIBITORS

(75) Inventors: Juan Francisco Caturla Javaloyes, Barcelona (ES); Graham Warrellow, Barcelona (ES)

(73) Assignee: Laboratorios Almirall, S.A., Barcelona (ES)

( * ) Notice: Subject to any disclaimer, the term of this patent is extended or adjusted under 35 U.S.C. 154(b) by 414 days.

(21) Appl. No.: 10/544,361

(22) PCT Filed: Feb. 12, 2004

(86) PCT No.: PCT/EP2004/001295

§ 371 (c)(1),
(2), (4) Date: Dec. 14, 2005

(87) PCT Pub. No.: WO2004/072058

PCT Pub. Date: Aug. 26, 2004

(65) Prior Publication Data

US 2006/0142380 A1 Jun. 29, 2006

(30) Foreign Application Priority Data

Feb. 13, 2003 (ES) .................................. 200300355

(51) Int. Cl.
*A61K 31/35* (2006.01)
*C07D 309/38* (2006.01)
(52) U.S. Cl. .................... 514/460; 514/336; 546/282.1; 549/60; 549/416; 549/417
(58) Field of Classification Search .................. 549/60, 549/416, 417; 546/282.1; 514/336, 460
See application file for complete search history.

(56) References Cited

U.S. PATENT DOCUMENTS

| 5,994,379 | A | 11/1999 | Bayly et al. |
| 6,231,888 | B1 | 5/2001 | Lerner et al. |
| 6,340,694 | B1 | 1/2002 | Joo et al. |
| 6,451,794 | B1 | 9/2002 | Beswick et al. |
| 6,486,194 | B2 | 11/2002 | Ducharme et al. |
| 6,492,416 | B1 | 12/2002 | Shin et al. |
| 6,518,303 | B2 | 2/2003 | Crespo Crespo et al. |
| 6,649,636 | B1 | 11/2003 | Ando et al. |
| 2002/0013318 | A1 | 1/2002 | Black et al. |
| 2002/0032230 | A1 | 3/2002 | Pal et al. |
| 2002/0045644 | A1 | 4/2002 | Crespo Crespo et al. |
| 2006/0189684 | A1 | 8/2006 | Javaloyes |
| 2006/0229338 | A1 | 10/2006 | Javaloyaes |

FOREIGN PATENT DOCUMENTS

| ES | 2 154 561 | 4/2001 |
| GB | 2 294 879 A | 5/1996 |
| WO | WO 96/08482 | 3/1996 |
| WO | WO 97/34882 | 9/1997 |
| WO | WO 97/44028 | 11/1997 |
| WO | WO 98/03484 | 1/1998 |
| WO | WO 99/14205 | 3/1999 |
| WO | WO 00/14083 | 3/2000 |
| WO | WO 00/18753 | 4/2000 |
| WO | WO 00/61571 | 10/2000 |
| WO | WO 01/00229 A1 | 1/2001 |
| WO | WO 01/68633 | 9/2001 |
| WO | WO 01/91856 | 12/2001 |
| WO | WO 02/09759 | 2/2002 |
| WO | WO 02/55502 | 7/2002 |
| WO | WO 03/006451 | 1/2003 |
| WO | WO 03/087062 | 10/2003 |
| WO | WO 04/72058 | 8/2004 |
| WO | WO 2004/072037 A1 | 8/2004 |
| WO | WO 2004/072057 A1 | 8/2004 |

OTHER PUBLICATIONS

Habeeb, Amgad G. et al., "Design and syntheses of diarylisoxazoles: novel inhibitors of cyclooxygenase-2 (cox-2) with analgesic-antiinflammatory activity," Drug Development Research, 51:273-286 (2000).

Padakanti, Srinivas et al., "A simple and rapid entry to 5-alkyl (aryl)-5-hydroxy-3,4-diarylfuranones and 3a-hydroxy-1-aryl-2,3a,4,5-tetrahydronaphthofuranones via a tandem esterification and oxidative cyclization process," Tetrahedron Letters, 43:8715-8719 (2002).

Joo, Yung Hyup, et al., "2,3-diarylbenzopyran derivatives as a novel class of selective cyclooxygenase-2 inhibitors," Bioorganic & Medicinal Chemistry Letters, 13:413-417 (2003).

Shin, Song Seok et al., "In vitro structure-activity relationship and in vivo studies for a novel class of cyclooxygenase-2 inhibitors: 5-aryl-2,2-dialkyl-4-phenyl-3(2h) furanone derivatives," J. Med. Chem., 47:792-804 (2004).

(Continued)

*Primary Examiner*—Bernard Dentz
(74) *Attorney, Agent, or Firm*—Finnegan, Henderson, Farabow, Garrett & Dunner, L.L.P.

(57) ABSTRACT

The present invention relates to 2-phenylpyran-4-derivatives of general formula (I), processes for their preparation, pharmaceutical compositions containing them, and their medical uses.

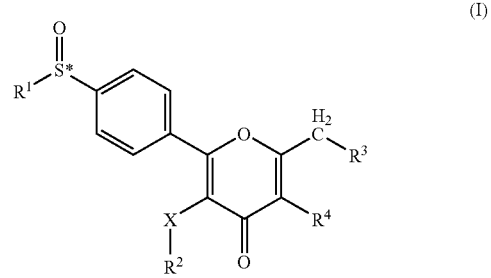

26 Claims, No Drawings

OTHER PUBLICATIONS

Moh, Joo Hyun et al., "A prodrug approach to COX-2 inhibitors with methylsulfone," *Bioorganic & Medicinal Chemistry Letters*, 14:1757-1760 (2004).

Chung, Shin, "COX-2 inhibitors with a methylsulfoxide pharmacophore," *Expert Opin. Ther. Patents*, 15(5):617-620 (2005).

Caturla, Francisco et al., "Racemic and chiral sulfoxides as potential prodrugs of the COX-2 inhibitors vioxx® and arcoxia®," *Bioorganic & Medicinal Chemistry Letters*, 16:3209-3212 (2006).

Caturla, Francisco et al., "Racemic and chiral sulfoxides as potential prodrugs of 4-pyrone COX2 inhibitors," *Bioorganic & Medicinal Chemistry Letters*, 16(13):3605-3608 (2006).

International Search Report for PCT/EP2004/001295, mailed on Jul. 8, 2004.

Forgione, P. et al. "Magnesium mediated carbometallation of propargyl alcohols: direct routes to furans and furanones," *Tetrahedron Letters* 41: 17-20 (2000).

Record for Entoricoxib from MedicaLook at http://www.medical-look.com/reviews/Etoricoxib.html, last accessed on Feb. 15, 2009.

International Search Report for PCT/EP2004/001297, mailed Jul. 8, 2004.

International Search Report for PCT/EP2004/001296, mailed on May 26, 2004.

Bennett, A. et al. "COX-2 inhibitors compared and contrasted," *Expert Opinion on Investigational Drugs* 2(11): 1859-1876 (2001).

Bishop-Bailey, D. et al. "Cyclooxygenase -2 in vascular smooth muscle," *International Journal of Molecular Medicine* 3(1): 41-48 (1999).

Elder, D. et al. "COX-2 inhibitors for colorectal cancer," *Nature Medicine* 4(4): 392-393 (1998).

Friesen, RW et al. "2-pyridinyl-3-(4-methylsulfonyl)phenylpyridines: selective and orally active cyclooxygenase-2 inhibitors," *Bioorganic & Medicinal Chemistry Letters* 8(19): 2777-2782 (1998).

Ho, L. et al. "The Potential of Selective COX-2 Inhibitors in Inflammatory and other Diseases," *Drugs of Today* 37(3): 181-185 (2001).

O'Banion, MK "COX-2 and Alzheimer's disease: potential roles in inflammation and neurodegeneration," *Expert Opinion on Investigational Drugs* 8(10): 1521-1531 (1999).

Office Action mailed Oct. 11, 2007, in co-pending U.S. Appl. No. 10/544,360, Examiner D. Gallis.

Office Action mailed Apr. 16, 2008, in co-pending U.S. Appl. No. 10/544,360, Examiner D. Gallis.

Office Action mailed Dec. 22, 2008, in co-pending U.S. Appl. No. 10/544,360, Examiner D. Gallis.

Office Action mailed Sep. 25, 2008, in co-pending U.S. Appl. No. 10/544,359, Examiner R. Covington.

Office Action mailed May 13, 2009, in co-pending U.S. Appl. No. 10/544,359, Examiner R. Covington.

Prasit, P., et al., "The discovery of rofecoxib, [MK 966, VIOXX®, 4-(4'-methylsulfonylphenyl)-3-phenyl-2(5h)-furnanone], an orally active cyclooxygenase-2 inhibitor," *Bioorganic & Medicinal Chemistry Letters*, 9:1773-1778 (1999).

Xie, W. "COX-2 and a New Generation of NSAIDS," *Frontiers of Biotechnology & Pharmaceuticals* 1:223-232 (2000).

2-PHENYLPYRAN-4-ONE DERIVATIVES AS SELECTIVE COX-2 INHIBITORS

This application is a national stage application under 35 U.S.C. § 371 of international application number PCT/EP2004/001295, filed on Feb 12, 2004, which claims the benefit of priority from Spanish application number ES 200300355, filed on Feb. 13, 2003.

This invention relates to new therapeutically useful 2-phenylpyran-4-one derivatives, to processes for their preparation, to pharmaceutical compositions containing them and to their use as medicaments.

It is known that non-selective inhibition of the enzyme cyclooxygenase (COX) prevents the overproduction of prostaglandins associated with inflammation, which is mediated by cyclooxygenase-2 (COX-2) but, at the same time, deprives tissues of basal levels of prostaglandins necessary for the health of certain tissues mediated largely by cyclooxygenase-1 (COX-1). Non steroidal anti-inflammatory drugs are non-selective inhibitors of COX and for that reason, have side effects of decreased renal blood flow, decreased platelet function, dyspepsia and gastric ulceration.

We have now found that certain 2-phenylpyran-4-one derivatives selectively inhibit COX-2 in preference to COX-1 and are useful in the treatment of COX-2 mediated diseases and their symptoms, such as inflammation, pain, fever, and asthma with fewer side effects.

Accordingly the present invention provides a 2-phenylpyran-4-one compound of formula (I):

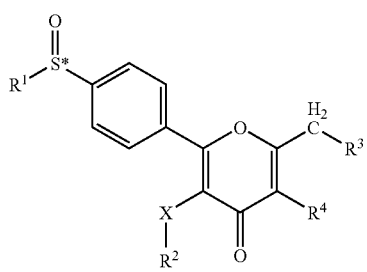

(I)

wherein:

$R^1$ represents an alkyl group;

$R^2$ represents an alkyl, $C_3$-$C_7$ cycloalkyl, pyridyl, thienyl, naphthyl, tetrahydronaphthyl or indanyl group, or a phenyl group which may be unsubstituted or substituted by one or more halogen atoms or alkyl, trifluoromethyl, hydroxy, alkoxy, methylthio, amino, mono- or dialkylamino, hydroxyalkyl or hydroxycarbonyl groups;

$R^3$ and $R^4$, which may be the same or different represent a hydrogen atom, or an alkyl, alkenyl or alkynyl group which may be unsubstituted or substituted by one or more halogen atoms; and X represents a single bond, an oxygen atom or a methylene group more preferably an oxygen atom;

or a pharmaceutically acceptable salt thereof.

The compounds of formula (I) have a chiral center at the sulfur atom of the sulfinyl group, shown by an asterisk (*) in the formula, and consequently exist in the form of the two different enantiomers if there are no other chiral centers in the compounds or in the form of various diastereomers should there be other chiral centers in the compounds. All these stereoisomeric compounds and their mixtures are encompassed in the present invention. The formulas used in the present description are intended to represent all possible stereoisomers or any mixture thereof.

In a preferred embodiment the invention provides a compound of formula (I) wherein $R^1$ represents an unsubstituted alkyl group, more preferably a methyl group.

In another embodiment the present invention provides a compound of formula (I) wherein X represents a single bond or an oxygen atom, more preferably an oxygen atom.

In still another embodiment the present invention provides a compound of formula (I) wherein $R^3$ represents a hydrogen atom or an unsubstituted $C_{1-3}$ alkyl group, preferably a hydrogen atom.

In yet another embodiment the present invention provides a compound of formula (I) wherein $R^2$ represents a branched alkyl, $C_3$-$C_7$ cycloalkyl, naphthyl, tetrahydronaphthyl or indanyl group, an unsubstituted phenyl group or a phenyl group substituted by one or more halogen atoms, alkyl groups and/or alkoxy groups; more preferably an unsubstituted phenyl group or a phenyl group substituted by 1, 2 or 3 substituents independently selected from halogen atoms, methoxy group or methyl groups; still more preferably a phenyl group substituted by 1 or 2 substituents independently selected from halogen atoms and methyl groups.

Most preferably $R^2$ represents an optionally substituted phenyl group of formula:

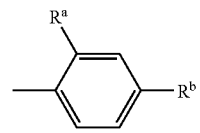

wherein $R^a$ and $R^b$ are selected from the group consisting of hydrogen atoms, halogen atoms, alkyl groups and/or alkoxy groups, more preferably halogen atoms and still more preferably $R^2$ is a 2,4-difluorophenyl, 4-chloro-2-fluorophenyl or 4-bromo-2-fluorophenyl group.

Unless otherwise specified the term alkyl as used herein embraces optionally substituted, linear or branched radicals having 1 to 20 carbon atoms or, preferably 1 to 12 carbon atoms. More preferably alkyl radicals are "lower alkyl" radicals having 1 to 8, preferably 1 to 6 and more preferably 1 to 4 carbon atoms.

Examples include methyl, ethyl, n-propyl, i-propyl, n-butyl, sec-butyl and tert-butyl, n-pentyl, 1-methylbutyl, 2-methylbutyl, isopentyl, 1-ethylpropyl, 1,1-dimethylpropyl, 1,2-dimethylpropyl, n-hexyl or 1-ethylbutyl, 2-ethylbutyl, 1,1-methylbutyl, 1,2-dimethylbutyl, 1,3-dimethylbutyl, 2,2-dimethylbutyl, 2,3-dimethylbutyl, 2-methylpentyl, 3-methylpentyl; iso-hexyl radicals.

A said optionally substituted alkyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Typically, substituents on an alkyl group are themselves unsubstituted.

When it is mentioned that alkyl radicals may be optionally substituted it is meant to include linear or branched alkyl radicals as defined above, which may be unsubstituted or substituted in any position by a one or more substituents, for example by 1, 2 or 3 substituents. When two or more substituents are present, said substituents may be the same or different As used herein, the term alkenyl embraces linear or branched, mono or polyunsaturated radicals having 2 to 20 carbon atoms or, preferably, 2 to 12 carbon atoms. More preferably alkenyl radicals are "lower alkenyl" radicals having 2 to 8, preferably 2 to 6 and more preferably 2 to 4 carbon atoms. In particular it is preferred that the alkenyl radicals are mono or diunsaturated.

Examples include vinyl, allyl, 1-propenyl, isopropenyl, 1-butenyl, 2-butenyl; 3-butenyl, 1-pentenyl, 2-pentenyl, 3-pentenyl and 4-pentenyl radicals.

When it is mentioned that alkenyl radicals may be optionally subsituted it is meant to include linear or branched alkenyl radicals as defined above, which may be unsubstituted or substituted in any position by one or more specified substituents, for example by 1, 2 or 3 substituents. When two or more substituents are present, said substituents may be the same or different.

A said optionally substituted alkenyl group is typically unsubstituted or substituted with 1, 2 or 3 substituents which may be the same or different. The substituents are selected from halogen atoms, preferably fluorine atoms.

As used herein, the term alkynyl embraces linear or branched, mono or polyunsaturated radicals having 2 to 20 carbon atoms or, preferably, 2 to 12 carbon atoms. More preferably, alkynyl radicals are "lower alkynyl" radicals having 2 to 8, preferably 2 to 6 and more preferably 2 to 4 carbon atoms. In particular, it is preferred that the alkynyl radicals are mono or diunsaturated.

Examples include 1-propynyl, 2-propynyl, 1-butynyl, 2-butynyl and 3-butynyl radicals.

When it is mentioned that alkynyl radicals may be optionally subsituted it is meant to include linear or branched alkynyl radicals as defined above, which may be unsubstituted or substituted in any position by one or more specified substituents, for example by 1, 2 or 3 substituents. When two or more substituents are present, said substituents may be the same or different.

A said optionally substituted alkynyl group is typically unsubstituted or substituted with 1, 2 or 3 substituents which may be the same or different. The substituents are selected from halogen atoms, preferably fluorine atoms.

As used herein, the term alkoxy (or alkyloxy) embraces optionally substituted, linear or branched oxy-containing radicals each having alkyl portions of 1 to 10 carbon atoms. More preferred alkoxy radicals are "lower alkoxy" radicals having 1 to 8, preferably 1 to 6 and more preferably 1 to 4 carbon atoms.

An alkoxy group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms.

Preferred alkoxy radicals include methoxy, ethoxy, n-propoxy, i-propoxy, n-butoxy, sec-butoxy, tbutoxy, trifluoromethoxy, difluoromethoxy, hydroxymethoxy, 2-hydroxyethoxy or 2-hydroxypropoxy.

As used herein, the term monoalkylamino embraces radicals containing an optionally substituted, linear or branched alkyl radical of 1 to 10 carbon atoms attached to a divalent-NH— radical. More preferred monoalkylamino radicals are "lower monoalkylamino" radicals having 1 to 8, preferably 1 to 6 and more preferably 1 to 4 carbon atoms.

A monoalkylamino group typically contains an alkyl group which is unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms.

Preferred optionally substituted monoalkylamino radicals include methylamino, ethylamino, n-propylamino, i-propylamino, nbutylamino, sec-butylamino, t-butylamino, trifluoromethylamino, difluoromethylamino, hydroxymethylamino, 2-hydroxyethylamino or 2-hydroxypropylamino.

As used herein, the term dialkylamino embraces radicals containing a trivalent nitrogen atom with two optionally substituted, linear or branched alkyl radicals of 1 to 10 carbon atoms attached thereto. More preferred dialkylamino radicals are "lower dialkylamino" radicals having 1 to 8, preferably 1 to 6 and more preferably 1 to 4 carbon atoms in each alkyl radical.

A dialkylamino group typically contains two alkyl groups, each of which is unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms.

Preferred optionally substituted dialkylamino radicals include dimethylamino, diethylamino, methyl(ethyl)amino, di(n-propyl)amino, n-propyl(methyl)amino, n-propyl(ethyl) amino, di(i-propyl)amino, i-propyl(methyl)amino, i-propyl (ethyl)amino, di(n-butyl)amino, n-butyl(methyl)amino, n-butyl(ethyl)amino, n-butyl(i-propyl)amino, di(sec-butyl) amino, sec-butyl(methyl)amino, sec-butyl(ethyl)amino, sec-butyl(n-propyl)amino, sec-butyl(i-propyl)amino, di(t-butyl) amino, t-butyl(methyl)amino, t-butyl(ethyl)amino, t-butyl(n-propyl)amino, t-butyl(i-propyl)amino, trifluoromethyl (methyl)amino, trifluoromethyl(ethyl)amino, trifluoromethyl(n-propyl)amino, trifluoromethyl-propyl) amino, trifluoromethyl(n-butyl)amino, trifluoromethyl(sec-butyl)amino, difluoromethyl(methyl)amino, difluoromethyl (ethyl)amino, difluoromethyl(n-propyl)amino, difluoromethyl(i-propyl)amino, difluoromethyl(n-butyl)) amino, difluoromethyl(sec-butyl)amino, difluoromethyl(t-butyl)amino, difluoromethyl(trifluornmethyl)amino, hydmxymethyl(methyl)amino, ethyl(hydroxymethyl)amino, hydroxymethyl(n-propyl)amino, hydroxym ethyl(i-propyl) amino, n-butyl(hydroxymethyl)amino, secbutyl(hydroxymethyl)amino, tutyl(hydroxymethyl)amino, difluoromethyl (hydroxymethyl)amino, hydroxymethyl(trifluoromethyl) amino, hydroxyethyl(methyl)amino, ethyl(hydroxyethyl) amino, hydroxyethyl(n-propyl)amino, hydroxyethyl(i-propyl)amino, n-butyl(hydroxyethyl)amino, sec-butyl (hydroxyethyl)amino, t-butyl(hydroxyethyl)amino, difluoromethyl(hydroxyethyl)amino, hydroxyethyl(trifluoromethyl)amino, hydroxypropyl(methyl)amind, ethyl(hydroxypropyl)amino, hydroxypropyl(n-propyl)amino, hydroxypropyl(i-propyl)amino, n-butyl(hydroxypropyl) amino, sec-butyl(hydroxypropyl)amino, t-butyl(hydroxypropyl)amino, difluoromethyl(hydroxypropyl)amino, hydroxypropyl(trifluoromethyl)amino.

As used herein, the term hydroxyalkyl embraces linear or branched alkyl radicals having 1 to 10 carbon atoms, preferably 1 to 6 carbon atoms, any one of which may be substituted with one or more hydroxyl radicals.

Examples of such radicals include hydroxymethyi, hydroxyethyl, hydroxypropyl, hydroxybutyl and hydroxyhexyl.

As used herein, the term cycloalkyl embraces saturated carbocyclic radicals and, unless otherwise specified, a cycloalkyl radical typically has from 3 to 7 carbon atoms.

A cycloalkyl radical is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. When a cycloalkyl radical carries 2 or more substituents, the substituents maybe the same or different.

Examples include cyclopropyl, cyclobutyl, cyclopentyl, cyclohexyl and cycloheptyl. It is preferably cyclopropyl, cyclopentyl or cyclohexyl. When a cycloalkyl radical carries 2 or more substituents, the substituents maybe the same or different.

As used herein, the term halogen atom embraces chlorine, fluorine, bromine or iodine atom typically a fluorine, chlorine or bromine atom, most preferably chlorine or fluorine. The term halo when used as a prefix has the same meaning.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkaline earth metal (e.g. calcium or magnesium) hydroxides and organic bases, for example alkyl amines, arylalkyl amines and heterocyclic amines.

In a phenyl group substituted by one or more halogen atoms or alkyl, trifluoroalkyl, hydroxy, alkoxy, methylthio, amino, mono- or dialkyl amino, hydroxyalkyl or hydroxycarbonyl groups, the phenyl ring may be substituted by 1, 2, 3, 4 or 5 substituents, preferably 1, 2 or 3 substituents, each being independently selected from the possible substituents set out above. That is to say, the phenyl group (attached to X or the pyran-4-one ring through its 1-position) may be substituted at any of the remaining positions, that is to say the 2, 3, 4, 5 or 6-positions. A phenyl group having more than one substituent may be substituted at any combination of positions. For example a phenyl group having two substituents may be substituted at the 2 and 3, 2 and 4, 2 and 5, 2 and 6, 3 and 4 or 3 and 5 positions.

Specific examples of the 2-phenylpyran-4-one derivatives of the present invention include:
  3-(2,4-Difluorophenoxy)-6-methyl-2-[4-(methylsulfinyl) phenyl]-4H-pyran-4-one
  3-(4-Chloro-2-fluorophenoxy)-6-methyl-2-[4(methylsulfinyl)phenyl]-4H-pyran-4-one
  3-(4-Bromo-2-fluorophenoxy)-6-methyl-2-[4-(methylsulfinyl)phenyl]-4H-pyran-4-one
  3-(2,4-difluorophenoxy)-6-ethyl-5-methyl-2-[(4-(methylsulfinylphenyl)]-4H-pyran-4-one;
  3-(4-fluoro-2-methylphenoxy)-6-methyl-2-[(4-(methysulfinyl)phenyl]-4H-pyran-4-one;
  3-(4-chloro-2-methylphenoxy)-6-methyl-2-[(4-(methylsulfinyl)phenyl]-4H-pyranone;
  3-(2-chloro-4-methylphenoxy)-6-methyl-2-[(4-methylsulfinyl)phenyl]-4H-pyran-4-one;
  3-(2-bromophenoxy)-6-methyl-2-[(4-(methylsulfinyl) phenyl]-4H-pyran-4-one;
  3-(3-bromophenoxy)-6-methyl-2-[(4-(methylsulfinyl) phenyl]-4H-pyran-4-one;
  3-(4-bromo-2-fluorophenoxy)-6-methyl-2-[(4-(methylsulfinyl)phenyl]-4H-pyran-4-one;
  3-(4-bromo-2-chlorophenoxy)-6-methy-2-[(4-(methylsulfinyl)phenyl]-4H-pyran-4-one;
  3-(2,4-dibromophenxy)-6-methyl-2-[(4-(methysuffinyl) phenyl]-4H-pyran-4-one;
  3(2,4-difluorophenoxy)-6-methyl-2-[(4-(ethylsulfinyl) phenyl]-4H-pyran-4-one;
  6-methyl-3-(2-methylphenoxy)-2-[(4-(methylsulfinyl) phenyl]H-pyran-4-one;
  6-methy-3-(3-methylphenoxy)-2-[(4-(methylsulfinyl) phenyl]-H-pyran-4-one;
  3-(2-fluoro-4-methylphenoxy)-6methyl-2-[(4-methylsulfinyl)phenyl]-4H-pyran-4-one;

in the form of all possible enantiomers and mixtures thereof and pharmaceutically acceptable salts thereof.

Of outstanding interest are compounds of formula:

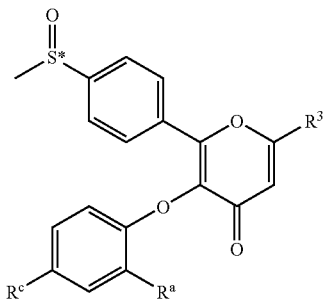

| Example | $R^3$ | $R^a$ | $R^c$ | Configuration |
|---------|-------|-------|-------|---------------|
| 1 | Me | F | F | Racemic |
| 2 | Me | F | F | Enantiomer 1a |
| 3 | Me | F | F | Enantiomer 1b |
| 4 | Me | F | Cl | Racemic |
| 5 | Me | F | Cl | Enantiomer 4a |
| 6 | Me | F | Cl | Enantiomer 4b |
| 7 | Me | F | Br | Racemic |
| 8 | Me | F | Br | Enantiomer 7a |
| 9 | Me | F | Br | Enantiomer 7b | in the form of all possible enantiomers and mixtures thereof and pharmaceutically acceptable salts thereof.

The present invention also provides processes for preparing a compound of formula (I)

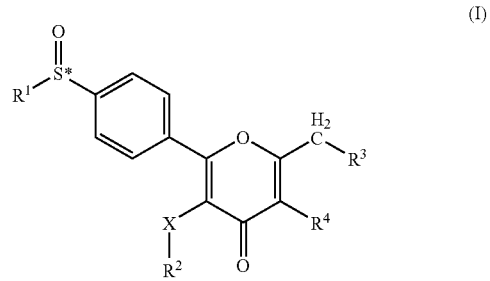

(I)

wherein $R^1$, $R^2$ $R^3$, $R^4$ and X are as defined above by reacting a mercapto derivative of formula (II):

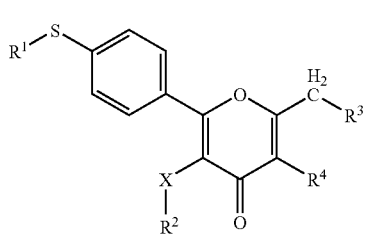

(II)

wherein $R^1$, $R^2$, $R^3$, $R^4$ and X are as defined above with an oxidizing agent, preferably sodium metaperiodate when it is desired to obtain racemic mixtures of compounds or using a mixture of titanium tetraisopropoxide, t-butyl hydroperoxide and either the (R,R) or the (S,S) forms of diethyl tartrate when it is desired to obtain mixtures of compounds of formula (I) enriched with compounds having a specific configuration at the sulfinyl chiral center.

The reaction between the mercapto derivative of formula (II) and the oxidizing agent is preferably carried out in an organic solvent, preferably a chlorinated solvent or a mixture of chlorinated solvents and $C_1$-$C_4$ alcohols at a temperature of from −25° C. to 40° C. It is preferred that the chlorinated solvent is selected from the group consisting of 1,2-dichloroethane, methylene chloride, chloroform and mixtures thereof. The $C_1$-$C_4$ alcohol is preferably selected from methanol and ethanol. Preferred solvent systems are 1,2-dichloroethane or a mixture of methylene chloride with methanol or ethanol.

The mercapto derivatives of formula (II) are known and can be prepared following the teachings of WO 01/68633 A1.

The 2-phenylpyran-4-one derivatives of formula (I) in which a basic group is present can be converted by methods known per se info pharmaceutically acceptable salts, preferably acid addition salts by treatment with organic or inorganic adds such as fumaric, tartaric, succinic or hydrochloric acid.

The following biological tests and data further illustrate this invention.

COX-1 and COX-2 Activities in Human Whole Blood

Fresh blood from healthy volunteers who had not taken any non-steroidal anti-inflammatory drugs for at least 7 days prior to blood extraction was collected in heparinized tubes (20 units of heparin per ml). For the COX-1 activity determination, 500 µl aliquots of blood were incubated with either 5 µl vehicle (dimethylsulphoxide) or 5 µl of a test compound for 24 h at 37° C. Calcium ionophore A23187 (25 µM) was added 20 min before stopping the incubation. Plasma was separated by centrifugation (10 min at 13000 rpm) and kept at −30° C. until $TXB_2$ levels were measured using an enzyme immunoassay kit (EIA).

The effect of the compounds was evaluated by incubating each compound at five to six different concentrations with triplicate determinations. $IC_{50}$ values were obtained by non-linear regression using InPlot, GraphPad software on an IBM computer.

For the COX-2 activity determination, 500 µl aliquots of blood were incubated in the presence of LPS (10 µg/ml) for 24 h at 37° C. in order to induce the COX-2 expression (Patriagnani et al., J. Pharm. Exper. Ther. 271; 1705-1712 (1994)). Plasma was separated by centrifugation (10 min at 13000 rpm) and kept at −30° C. until $PGE_2$ levels were measured using an enzyme immunoassay kit (EIA). The effects of inhibitors were studied by incubating each compound (5 µl aliquots) at five to six different concentrations with duplicate determinations in the presence of LPS for 24 hours. $IC_{50}$ values were obtained by non-linear regression using InPlot, GraphPad software on an IBM computer.

The results obtained from the biological assays are shown in Table 1.

TABLE 1

| | COX-1 and COX-2 Inhibition | | |
|---|---|---|---|
| Example | COX-1 $IC_{50}$ (µM) | COX-2 $IC_{50}$ (µM) | Ratio COX-1/COX-2 |
| 1 | 100 | 0.96 | 104 |
| 2 | 100 | 2.1 | 48 |
| <u>3</u> | <u>86.6</u> | <u>0.27</u> | <u>321</u> |
| <u>4</u> | 81, 1.3 | 0.37 | 219 |
| 5 | 72.9 | 2.47 | 30 |
| 6 | 100 | 0.25 | 400 |
| 7 | <u>77.0</u> | <u>0.57</u> | <u>135</u> |
| 8 | 32.1 | 1.58 | 20 |
| 9 | 73.1 | 0.17 | 430 |

As shown in Table 1, the 2-phenylpyran-4-one derivatives of formula (I) are potent and selective COX-2 inhibitors. Thus the compounds of the invention are preferably selective inhibitors of mammalian COX-2, for example human COX-2.

The compounds of the invention also preferably have low inhibitory activity toward mammalian COX-1, for example human COX-1. Inhibitory activity can typically be measured by in vitro assays, for example as described above. Some of the compounds of the present invention have also shown an unexpected pharmacokinetic profile.

Preferred compounds of the invention have an $IC_{50}$ value for COX-2 of less than 50 µM, preferably less than 10 µM more preferably less than 5 µM, still more preferably less than 2,5 µM. Preferred compounds of the invention also have an $IC_{50}$ value for COX-1 of greater than 10 µM, preferably greater than 20 µM. As an indicator of selectivity for inhibition of COX-2 over COX-1, the ratio of COX-1/COX-2 $IC_{50}$ values is preferably greater than 10, more preferably greater than 20, still more preferably greater than 50.

The present invention further provides a compound of formula (I) for use in a method of treatment of the human or animal body by therapy, in particular for the treatment of pain, fever or inflammation, to inhibit prostanoid-induced smooth muscle contraction or for the prevention or treatment of colorectal cancer or neurodegenerative diseases, for example, Alzheimer's disease.

The present invention further provides the use of a compound of formula (I) in the manufacture of a medicament for the treatment of pain, fever or inflammation, to inhibit prostanolid-induced smooth muscle contraction or for the prevention or treatment of colorectal cancer.

The compounds of formula (I) are useful for relief of pain, fever and inflammation of a variety of conditions including rheumatic fever, symptoms associated with influenza or other viral infections, common cold, low back and neck pain, dysmenorrhoea, headache, toothache, sprains and strains, myositis, neuralgia, synovitis, bursitis, tendinitis, injuries, following surgical and dental procedures and arthritis including rheumatoid arthritis, osteoarthritis, gouty arthritis, spondyloarthopathies, systemic lupus erythematosus and juvenile arthritis. They may also be used in the treatment of skin inflammation disorders such as psoriasis, eczema, burning and dermatitis. In addition, such compounds may be used for the prevention or treatment of colorectal cancer or neurodegenerative diseases, for example, Alzheimer's disease.

The compounds of formula (I) will also inhibit prostanoid-induced smooth muscle contraction and therefore may be used in the treatment of dysmenorrhoea, premature labour, asthma and bronchitis.

The compounds of formula (I) can be used as alternative to conventional non-steroidal anti-inflammatory drugs, particularly where such non-steroidal anti-inflammatory drugs may be contraindicated such as the treatment of patients with gastrointestinal disorders including peptic ulcers, gastritis, regional enteritis, ulcerative colitis, diverticulitis, Crohn's disease, inflammatory bowel syndrome and irritable bowel syndrome, gastrointestinal bleeding and coagulation disorders, kidney disease (e.g. impaired renal function), those prior to surgery or taking anticoagulants, and those susceptible to non-steroidal anti-inflammatory drugs induced asthma.

The compounds can further be used to treat inflammation in diseases such as vascular diseases, migraine headaches, periarteritis nodosa, thyroiditis, aplastic anaemia, Hodgkin's disease, scleroderma, type I diabetes, myasthenia gravis,, sarcoidosis, nephrotic syndrome, Behcet's syndrome, polymyositis, hypersensitivity, conjunctivitis, gingivitis and myocardial ischaemia.

Compounds of the present invention are inhibitors of cyclooxygenase-2 enzyme and are thereby useful to treat the cyclooxygenase-2 mediated diseases enumerated above.

Accordingly, the compounds of the present invention and pharmaceutically acceptable salts thereof, and pharmaceutical compositions comprising such compounds and/or salts thereof, may be used in a method of treatment of disorders of the human body which comprises administering to a patient requiring such treatment an effective amount of such a compound or a pharmaceutically acceptable salt thereof.

The present invention also provides pharmaceutical compositions, which comprise, as an active ingredient, at least a 2-phenylpyran-4-one derivative of formula (I) or a pharmacologically acceptable salt thereof in association with a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application.

Preferably the compositions are made up in a form suitable for oral, topical, nasal, inhalation, rectal, percutaneous or injectable administration.

The pharmaceutically acceptable excipients that are admixed with the active compound or salts of such compound, to form the compositions of this invention are known per se and the actual excipients used depend inter alia on the intended method of administering the compositions.

Compositions of this invention are preferably adapted for injectable and per os administration. In this case, the compositions for oral administration may take the form of tablets, retard tablets, sublingual tablets, capsules or liquid preparations, such as mixtures, elixirs, syrups or suspensions, all containing the compound of the invention; such preparations may be made by methods well-known in the art.

The diluents that may be used in the preparation of the compositions include those liquid and solid diluents that are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 10-600 mg of active ingredient per day. Daily dosage may be administered in one or more treatments, preferably from 1 to 4 treatments, per day.

The invention is illustrated by the following Preparations and Examples, which do not limit the scope of the invention in any way.

Preparation 1

3-(2,4-Difluorophenoxy)-6-methyl-2-[4-methylthio) phenyl]-4H-pyran-4-one

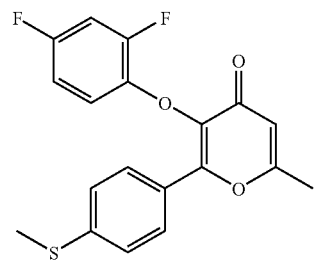

a) To a solution of 2,4-difluorophenol (1.04 g; 8 mmol) and 2-bromo-1-[4-(methylthio)phenyl]ethanone (1.96 9, 8 mmol) in methylene chloride (13 ml) was added a solution of potassium carbonate (1.66 g) and tetrabutylammonium hydrogensulfate (0.14 9) in water (5 ml). The mixture was stirred at room temperature for 16 hours. Water (100 ml) was added, the organic phase was decanted, and the basic phase was extracted with methylene chloride (2×100 ml). The organic solution was dried ($Na_2SO_4$) and the solvent removed under reduced pressure. The resulting solid was washed with ethyl ether. 2-(2,4-Difluorophenoxy)-1-[4-(methylthio)phenyl]ethanone was obtained (1.69 g, 72%) as an off-white solid.

b) The above compound (1.68 9, 5.7 mmol) was added to a solution of polyphosphoric acid (19 g) in acetic anhydride (8.5 ml), pre-heated at 9-100° C. The mixture was heated at the same temperature for 5 hours. After cooling, the reaction was poured into ice-water, extracted with ethyl acetate (3×100 ml), the organic solution was washed with saturated sodium bicarbonate (2×100 ml), water and brine, dried ($Na_2SO_4$), and the solvent removed under reduced pressure. The residual oil was purified by column chromatography with silica gel and ethyl acetate/n-hexane (1/1) as eluent. 3-(2,4-Difluorophenoxy)-6-methyl-2-[4-(methylthio)phenyl]4H-pyran-4-one (0.37 g, 17%) was obtained as an off-white solid.

δ (DMSO): 2.41 (s, 3H), 2.50 (s, 3H), 6.40 (s, 1H), 6.94 (m, 2H), 7.39 (m, 3H), 7.76 (d, J=8.4 Hz, 2H).

Preparation 2

3-(4-Chloro-2-fluorophenoxy)-6-methyl-2-[4-(methylthio)phenyl]-4H-pyran-4-one

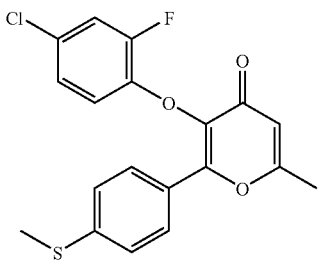

Obtained as an off-white solid (16% overall) from 2bromo-1-[4-(methylthio)phenyl]-ethanone and 4-chloro-2-fluorophenol by the procedure described in Preparation 1.

δ (DMSO): 2.42 (s, 3H), 2.50 (s, 3H), 6.30 (s, 1H), 6.73 (dd, $J_{HH}=J_{HF}=9.0$ Hz, 1H), 6.94 (m, 1H), 7.14 (dd, J=10.5, 2.4 Hz, 1H), 7.27 (d, J=8.7 Hz, 2H), 7.82 (d, J=8.7 Hz, 2H).

Preparation 3

3-(4-Bromo-2-fluorophenoxy)-6-methyl-2-[4-methylthio)phenyl]-4H-pyran-4-one

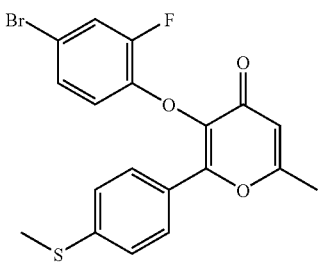

Obtained as an off-white solid (17% overall) from 2-bromo-1-[4-(methylthio)phenyl]-ethanone and 4-bromo-2-fluorophenol by the procedure described in Preparation 1.

δ (DMSO): 2.42 (s, 3H), 2.50 (s, 3H), 6.31 (s, 1H), 6.68 (dd, $J_{HH}=J_{HF}=8.7$ Hz, 1H), 7.07 (m, 1H), 7.26-7.30 (m, 3H), 7.82 (d, J=8.7 Hz, 2H).

EXAMPLE 1

3-(2,4-Difluorophenoxy)-6-methyl-2-[4-(methylsulfinyl)phenyl]-4H-pyran4-one

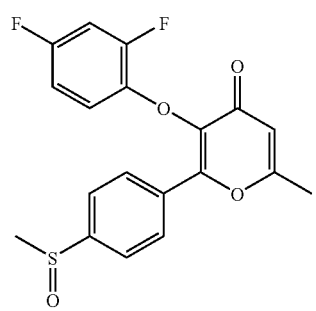

To a solution of the title compound of Preparation 1 (1.36 g, 3.8 mmol) in methanol (17 ml) was added dropwise a solution of sodium metaperiodate (0.80 g) in water (10 ml) at 0° C. and this mixture was stirred at this temperature for 2 h and 3 d at r.t. Then, the reaction was poured into water, extracted with ethyl acetate (3×100 ml), the organic solution dried (Na$_2$SO$_4$), and the solvent removed under reduced pressure. The residue was purified by column chromatography with silica gel and dichloromethane/ethyl acetate/methanolacetic acid (78/17/3/2) as eluent. 3-(2,4-Difluorophenoxy)-6-methyl-2-[4-(methylsulfinyl)phenyl]-4H-pyran-4-one (1.09 g, 77%) was obtained as an off-white solid.

m.p.: 158-159° C.

δ (DMSO): 2.44 (s, 3H), 2.76 (s, 3H), 6.32 (s, 1H), 6.67-6.92 (m, 3H), 7.74 (d, J=6.8 Hz, 2H), 8.08 (d, J=6.8 Hz, 2H).

EXAMPLE 2

3-(2,4-Difluorophenoxy)-6-methyl-2-[4-(methylsulfinyl)phenyl]-4H-pyran-4-one-Enantiomer 1a To a stirred solution of titanium tetraisopropoxide (1.05 ml, 3.5 mmol) and (R,R)-diethyl tartrate (2.45 ml, 14.2 mmol) in dry 1,2-dichloroethane (25 ml) cooled to –20° C. were added successively t-butyl hydroperoxide 5.5 M in nonane (1.29 ml, 7.1 mmol) and the title compound of Preparation 1 (1.26 g, 3.5 mmol) The mixture was stirred at –20° C. for 5 h, then washed with a 5% aqueous solution of sodium sulfite (50 ml) and brine. The organic layer was dried (Na$_2$SO$_4$) and the solvent removed under reduced pressure. The residue was purified by flash chromatography and ethyl acetate/methanol (95/5) as eluent. 3-2,4-Difluorophenoxy)-6-methyl-2-[4-methylsulfinyl)phenyl]-4H-pyran-4-one (0.18 g, 17%, 100% ee) was obtained as an off-white solid.

$[\alpha]_D^{22}=+82.3$ (c 0.25, MeOH)

m.p.: 158-159° C.

δ (DMSO): 2.44 (s, 3H), 2.76 (s, 3H), 6.32 (s, 1 H), 6.67-6.92 (m, 3H), 7.7(d, J=6.8 Hz, 2H), 8.08 (d, J=6.8 Hz, 2H).

EXAMPLE 3

3-(2,4-Difluorophenoxy)-6-methyl-2-[4-(methylsulfinyl)phenyl]-4H-pyran4-one-Enantiomer 1b Obtained as an off-white solid (57%, 88.4% ee) from the title compound of Preparation 1 and (S,S)-diethyl tartrate by the procedure described in Example 2.

$[\alpha]_D^{22}=-71.5$ (c 0.25, MeOH)

m.p.: 158-159° C.

δ (DMSO): 2.44 (s, 3H), 2.76 (s, 3H), 6.32 (s, 1H), 6.67-6.92 (m, 3H), 7.74 (d, J=6.8 Hz, 2H), 8.08 (d, J=6.8 Hz, 2H).

EXAMPLE 4

3-(4-Chloro-2-fluorophenoxy)-6-methyl-2-[4-(methylsulfinyl)phenyl]-4H-pyran-4-one

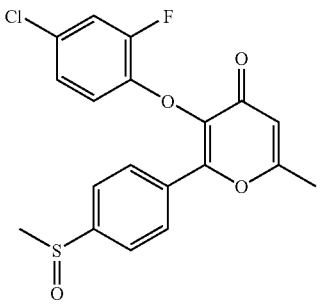

Obtained as an off-white solid (55%) from the title compound of Preparaition 2 and sodium metaperiodate by the procedure described in Example 1.

m.p.: 186-188° C.

δ (DMSO): 2.43 (s, 3H), 2.78 (s, 3H), 6.47 (s, 1H), 7.03-7.15 (m, 2H), 7.56 (dd, J=10.8, 2.4 Hz, 1H), 7.84 (d, J=8.6 Hz, 2H), 7.99 (d, J=8.6 Hz, 2H).

EXAMPLE 5

3-4-Chloro-2-fluorophonoxy)-6-methyl-2-[4-(methylsuffinyl)phenyl]-4H-pyran-4-one-Enantiomer 4a Obtained as an off-white solid (48%, 100% ee) from the title compound of Preparation 2 and (R,R)-diethyl tartrate by the procedure described in Example 2.

$[\alpha]_D^{22}$=+77.7 (c 0.25, MeOH)

m.p.: 186-188° C.

δ (DMSO): 2.43 (s, 3H), 2.78 (s, 3H), 6.47 (s, 1H), 7.03-7.15 (m, 2H), 7.56 (dd, J=10.8, 2.4 Hz, 1H), 7.84 (d, J=8.6 Hz, 2H), 7.99 (d, J=8.6 Hz, 2H).

EXAMPLE 6

3-(4-Chloro-2-fluorophenoxy)-6-methyl-2-[4-(mefltylsulfinyl)phenyl]-4H-pyran-4-one-Enantiomer 4b Obtained as an off-white solid (49%, 98.4% ee) from the title compound of Preparation 2 and (S,S)-diethyl tartrate by the procedure described in Example 2.

$[\alpha]_D^{22}$=−77.0 (c 0.25, MeOH)

m.p.: 186-188° C.

δ (DMSO): 2.43 (s, 3H), 2.78 (s, 3H), 6.47 (s, 1H), 7.03-7.15 (m, 2H), 7.56 (dd, J=10.8, 2.4 Hz, 1 H), 7.84 (d, J=8.6 Hz, 2H), 7.99 (d, J=8.6 Hz, 2H).

EXAMPLE 7

3-(4-Bromo-2-fluorophenoxy)-6-methyl-2-[4-(methylsulfinyl)phenyl]-4H-pyran-4-one

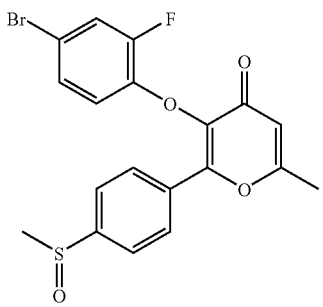

Obtained as an off-white solid (43%) from the title compound of Preparation 3 and sodium metaperiodate by the procedure described in Example 1.

m.p.: 201° C.

δ (DMSO): 2.43 (s, 3H), 2.78 (s, 3H), 6.47 (s, 1H), 7.01 (dd, $J_{HH}$=$J_{HF}$=9.0 Hz, 1 H), 7.24 (m, 1H), 7.66 (dd, J=10.8, 2.1 Hz, 1H), 7.84 (d, J=8.7 Hz, 2H), 7.98 (d, J=8.7 Hz, 2H).

EXAMPLE 8

3-4-Bromo-2-fluorophenoxy)-6-methyl-2-[4-methylsulfinyl)phenyl]-4H-pyran4-one-Enantiomer 7a Obtained as an off-white solid (48%, 98.8% ee) from the title compound of Preparation 3 and (R,R)diethyl tartrate by the procedure described in Example 2.

$[\alpha]_D^{22}$=+68.0 (c 0.5, MeOH)

m.p.: 201° C.

δ (DMSO): 2.43 (s, 3H), 2.78 (s, 3H), 6.47 (s, 1H), 7.01 (dd, $J_{HH}$=$J_{HF}$=9.0 Hz, 1H), 7.24 (m, 1H), 7.66 (dd, J=10.8, 2.1 Hz, 1H), 7.84 (d, J=8.7 Hz, 2H), 7.98 (d, J=8.7 Hz, 2H).

EXAMPLE 9

3-4-Bromo-2-fluorophenoxy)-6-methyl-2-[4-(methylsulfinyl)phenyg]4H-pyran-4-one-Enantiomer 7b Obtained as an off-white solid (53%, 98.2% ee) from the title compound of Preparation 3 and (S,S)-diethyl tartrate by the procedure described in Example 2.

$[\alpha]_D^{22}$=−71.3 (c 0.5, MeOH)

m.p.: 201° C.

δ (DMSO): 2.43 (s, 3H), 2.78 (s, 3H), 6.47 (s, 1H), 7.01 (dd, $J_{HH}$=$J_{HF}$=9.0 Hz, 1H), 7.24 (m, 1H), 7.66 (dd, J=10.8, 2.1 Hz, 1H), 7.84 (d, J=8.7 Hz, 2H), 7.98 (d, J=8.7 Hz, 2H).

EXAMPLE 10

Capsules 25,000 capsules each containing 100 mg of 3(2,4-Difluorophenoxy)-6-methyl-2-[4-(methylsulfinyl)phenyl]-4H-pyran-4-one (active ingredient) were prepared according to the following formulation:

| | |
|---|---|
| Active ingredient | 2.5 Kg |
| Lactose monohydrate | 5 Kg |
| Colloidal silicon dioxide | 0.05 Kg |
| Corn starch | 0.5 Kg |
| Magnesium stearate | 0.1 Kg |

Procedure

The above ingredients were sieved through a 60 mesh sieve, and were loaded into a suitable mixer and filled into 25,000 gelatine capsules.

EXAMPLE 11

Tablets 100,000 Tablets each containing 50 mg of 3-(2,4-Difluorophenoxy)-6-methyl-2-[4-(methylsulfinyl)phenyl]-4H-pyran-4-one (active ingredient) were prepared from the following formulation:

| | |
|---|---|
| Active ingredient | 5 Kg |
| Spray dried lactose | 19.9 Kg |
| Microcrystalline cellulose | 3.9 Kg |
| Sodium stearyl fumarate | 0.2 Kg |
| Colloidal silicon dioxide | 0.2 Kg |
| Carboxymethyl starch | 0.8 Kg |

Procedure

All the powders were passed through a screen with an aperture of 0.6 mm, then mixed in a suitable mixer for 20 minutes and compressed into 300 mg tablets using 9 mm disc and flat bevelled punches. The disintegration time of the tablets was about 3 minutes.

The invention claimed is:

1. A compound of formula (I):

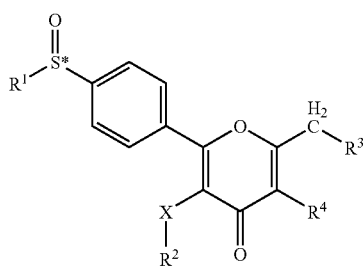

(I)

wherein $R^1$ represents an alkyl group;

$R^2$ represents a group chosen from alkyl, $C_3$-$C_7$ cycloalkyl, pyridyl, thienyl, naphthyl, tetrahydronaphthyl, indanyl, and a phenyl group; wherein the phenyl group is unsubstituted or substituted by one or more substituents independently chosen from halogen atoms, alkyl, trifluoromethyl, hydroxy, alkoxy, methylthio, amino, mono- and dialkylamino, hydroxyalkyl and hydroxycarbonyl groups;

$R^3$ and $R^4$, which may be the same or different, represent, independently of each other, a group chosen from a hydrogen atom, alkyl, alkenyl and alkynyl groups, wherein the alkyl, alkenyl, and alkynyl groups are unsubstituted or substituted by one or more halogen atoms; and X represents a single bond, an oxygen atom, or a methylene group;

, or a pharmaceutically acceptable salt thereof, in any enantiomeric form, or a mixture of any such compounds in any ratio.

2. A compound according to claim 1 wherein $R^1$ represents an unsubstituted alkyl group.

3. A compound according to claim 2 wherein $R^1$ is a methyl group.

4. A compound according to claim 1, wherein X represents an oxygen atom.

5. A compound according to claim 1, wherein $R^3$ and $R^4$ each represent, independently of each other, a hydrogen atom or an unsubstituted $C_{1-3}$ alkyl group.

6. A compound according to claim 5, wherein $R^3$ and $R^4$ each represent a hydrogen atom.

7. A compound according to claim 1, wherein $R^2$ is chosen from branched alkyl, $C_3$-$C_7$ cycloalkyl, naphthyl, tetrahydronaphthyl, indanyl, an unsubstituted phenyl group, and a phenyl group substituted by one or more substituents independently chosen from halogen atoms, alkyl groups and alkoxy groups.

8. A compound according to claim 7, wherein $R^2$ is an unsubstituted phenyl group or a phenyl group substituted by 1, 2 or 3 substituents independently chosen from halogen atoms, methoxy group and methyl groups.

9. A compound according to claim 8, wherein $R^2$ represents a phenyl group substituted by 1 or 2 substituents independently chosen from halogen atoms and methyl groups.

10. A compound according to claim 9, wherein $R^2$ represents an optionally substituted phenyl group of formula

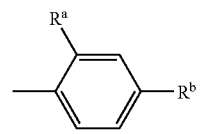

wherein $R^a$ and $R^b$ are independently chosen from hydrogen atoms, halogen atoms, alkyl groups and alkoxy groups.

11. A compound according to claim 10, wherein $R^a$ and $R^b$ are independently chosen from halogen atoms.

12. A compound according to claim 11, wherein $R^2$ is a 2,4-difluorophenyl, a 4-chloro-2-fluorophenyl or a 4-bromo-2-fluorophenyl group.

13. A compound according to claim 1, chosen from:
3-(2,4-Difluorophenoxy)-6-methyl-2-[4-(methylsulfinyl)phenyl]-4H-pyran-4-one;

3-(4-Chloro-2-fluorophenoxy)-6-methyl-2-[4-(methylsulfinyl)phenyl]-4H-pyran-4-one;
3-(4-Bromo-2-fluorophenoxy)-6-methyl-2-[4-(methylsulfinyl)phenyl]-4H-pyran-4-one;
3-(2,4-difluorophenoxy)-6-ethyl-5-methyl-2-[(4-(methylsulfinylphenyl)]-4H-pyran-4-one;
3-(4-fluoro-2-methylphenoxy)-6-methyl-2-[(4-(methylsulfinyl)phenyl]-4H-pyran-4-one;
3-(4-chloro-2-methylphenoxy)-6-methyl-2-[(4-(methylsulfinyl)phenyl]-4H-pyran-4-one;
3-(2-chloro-4-methylphenoxy)-6-methyl-2-[(4-(methylsulfinyl)phenyl]-4H-pyran-4-one;
3-(2-bromophenoxy)-6-methyl-2-[(4.-(methylsulfinyl)phenyl]-4H-pyran-4-one;
3-(3-bromophenoxy)-6-methyl-2-[(4-(methylsulfinyl)phenyl]-4H-pyran-4-one;
3-(4-bromo-2-fluorophenoxy)-6-methyl-2-[(4-(methylsulfinyl)phenyl]-4 H-pyran-4-one;
3-(4-bromo-2-chlorophenoxy)-6-methyl-2-[(4-(methylsulfinyl)phenyl]-4 H-pyran-4-one;
3-(2,4-dibromophenoxy)-6-methyl-2-[(4-(methylsulfinyl)phenyl]-4H-pyran-4-one;
3-(2,4-difluorophenoxy)-6-methyl-2-[(4-(ethylsulfinyl)phenyl]-4 H-pyran-4-one;
6-methyl-3-(2-methylphenoxy)-2-[(4-(methylsulfinyl)phenyl]-4H-pyran-4-one;
6-methyl-3-(3-methylphenoxy)-2-[(4-(methylsulfinyl)phenyl]-4H-pyran-4-one;
3-(2-fluoro-4-methylphenoxy)- 6-methyl-2-[(4-(methylsulfinyl)phenyl]-4H-pyran-4-one;
and pharmaceutically acceptable salts thereof, in any enantiomeric form, or a mixture of any such compounds in any ratio.

14. A compound according to claim 1, wherein the sulphur atom of the sulfinyl group has the (S) configuration.

15. A compound according to claim 1, wherein the sulphur atom of the sulfinyl group has the (R) configuration.

16. A compound according to claim 1, chosen from:
3-(2,4-Difluorophenoxy)-6-methyl-2-[4-(methylsulfinyl)phenyl]-4H-pyran-4-one;
3-(4-Chloro-2-fluorophenoxy)-6-methyl-2-[4-(methylsulfinyl)phenyl]-4H-pyran-4-one;
3-(4-Bromo-2-fluorophenoxy)-6-methyl-2-[4-(methylsulfinyl)phenyl]-4H-pyran-4-one;
wherein the compound is in the form of an enantiomer in the configuration designated 1b, 4b and 7b;
or a mixture thereof, or a pharmaceutically acceptable salt thereof.

17. A process for producing a compound as claimed in claim 1, comprising:
reacting a mercapto derivative of formula (II):

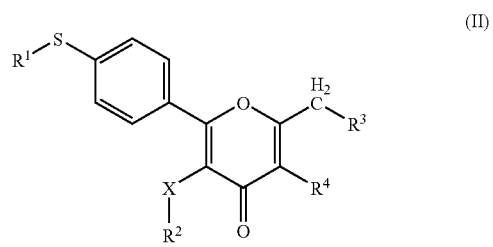

with an oxidizing agent to produce a compound of formula (I); and
optionally converting the compound of formula (I) into a pharmaceutically acceptable salt.

18. A process according to claim 17, wherein the oxidizing agent is chosen from:
(a) sodium metaperiodate; and
(b) a mixture of titanium tetraisopropoxide, t-butyl hydroperoxide and either the (R,R) or the (S,S) form of diethyl tartrate.

19. A process according to claim 18, wherein the reaction takes place in at least one chlorinated solvent or in a mixture of at least one chlorinated solvent and at least one $C_1$-$C_4$ alcohol.

20. A process according to claim 19; wherein the at least one chlorinated solvent is chosen from 1,2-dichloroethane, methylene chloride, chloroform and mixtures thereof.

21. A pharmaceutical composition comprising at least one compound according to claim 1 and at least one pharmaceutically acceptable carrier or diluent.

22. A method for treating pain, fever or inflammation, comprising administering to a human or animal subject in need of treatment an effective amount of a compound according to claim 1.

23. A medicament comprising at least one compound according to claim 1.

24. A method for treating pain, fever or inflammation, comprising administering to a human or animal subject in need of treatment an effective amount of a composition according to claim 21.

25. A method for inhibiting prostanoid-induced smooth muscle contraction or treating colorectal cancer, comprising administering to a human or animal subject in need of treatment an effective amount of a compound according to claim 1.

26. A method for inhibiting prostanoid-induced smooth muscle contraction or treating colorectal cancer, comprising administering to a human or animal subject in need of treatment an effective amount of a composition according to claim 21.

* * * * *